United States Patent
Suryakiran et al.

(10) Patent No.: US 12,195,240 B2
(45) Date of Patent: Jan. 14, 2025

(54) PACKAGE FOR MEDICAL DEVICES INCLUDING A PINCH-OPEN CLOSURE

(71) Applicant: Becton, Dickinson and Company, Franklin Lakes, NJ (US)

(72) Inventors: Thotapalli Suryakiran, Bangalore (IN); Sai Goutham Nuvvula, Guntur (IN); Sriram R, Kumbakonam (IN)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 18/093,187

(22) Filed: Jan. 4, 2023

(65) Prior Publication Data

US 2024/0217706 A1   Jul. 4, 2024

(51) Int. Cl.
  *B65D 33/16*   (2006.01)
  *A61B 50/30*   (2016.01)

(52) U.S. Cl.
  CPC .......... *B65D 33/16* (2013.01); *A61B 50/3001* (2016.02); *A61B 2050/314* (2016.02); *B65D 2251/1066* (2013.01); *B65D 2251/20* (2013.01)

(58) Field of Classification Search
  CPC .............. B65D 33/1625; B65D 33/165; B65D 33/1666; B65D 33/1675; B65D 33/1658; B65D 33/007; B65D 33/16; B65D 33/30; A61B 50/3001; A61B 50/20; A61B 50/36; A61B 2050/3013; A61B 2050/314; A61B 2050/316; A61B 2050/318; A61B 2050/0067; A61B 2050/007; A61B 30/3001; A61M 25/02

USPC ........................ 383/33, 34, 34.1, 43; 206/438
  See application file for complete search history.

(56) References Cited

U.S. PATENT DOCUMENTS

| | | | |
|---|---|---|---|
| 2,008,314 A | 7/1935 | Russell | |
| 3,272,248 A | 9/1966 | O'Farrell | |
| 4,909,881 A * | 3/1990 | Garland | .................. B32B 27/08 |
| | | | 156/244.14 |
| 5,044,774 A | 9/1991 | Bullard et al. | |
| 6,019,770 A | 2/2000 | Christoudias | |

(Continued)

FOREIGN PATENT DOCUMENTS

| | | |
|---|---|---|
| AU | 2017202762 B2 | 5/2017 |
| EP | 2571782 B1 | 9/2015 |

(Continued)

*Primary Examiner* — Jes F Pascua
*Assistant Examiner* — Nina K Attel
(74) *Attorney, Agent, or Firm* — The Webb Law Firm

(57) ABSTRACT

A package includes a flexible body configured to transition between a collapsed configuration and an expanded configuration. The body includes an open first end, a closed second end, and sides extending between the first end and the second end. The package also includes a closure connected to the body having a first end, a second end, and a slit extending at least partially between the first end and the second end of the closure. The closure is configured to transition between a closed configuration, in which the closure retains the body in the collapsed configuration sealing the open first end of the body, and an open configuration upon application of a biaxial force to the first end and the second end of the closure, which causes the body to transition to the expanded configuration.

19 Claims, 6 Drawing Sheets

(56) References Cited

U.S. PATENT DOCUMENTS

| | | | |
|---|---|---|---|
| 6,345,911 B1* | 2/2002 | Young | B65D 33/10 |
| | | | 383/44 |
| 7,300,207 B2 | 11/2007 | Linneweil | |
| 7,921,959 B2* | 4/2011 | Statner | A61B 46/10 |
| | | | 181/131 |
| 9,139,038 B1 | 9/2015 | Trollen | |
| 2002/0069615 A1* | 6/2002 | Gifford | B65D 47/286 |
| | | | 383/200 |
| 2005/0211590 A1* | 9/2005 | McClure | A61M 25/02 |
| | | | 206/441 |
| 2012/0141048 A1 | 6/2012 | Ribi | |
| 2016/0236826 A1* | 8/2016 | Hoskins | B65D 33/1675 |

FOREIGN PATENT DOCUMENTS

| | | |
|---|---|---|
| JP | 200372779 A | 3/2003 |
| RU | 2626712 C2 | 7/2017 |
| WO | 2010142744 A1 | 12/2010 |

* cited by examiner

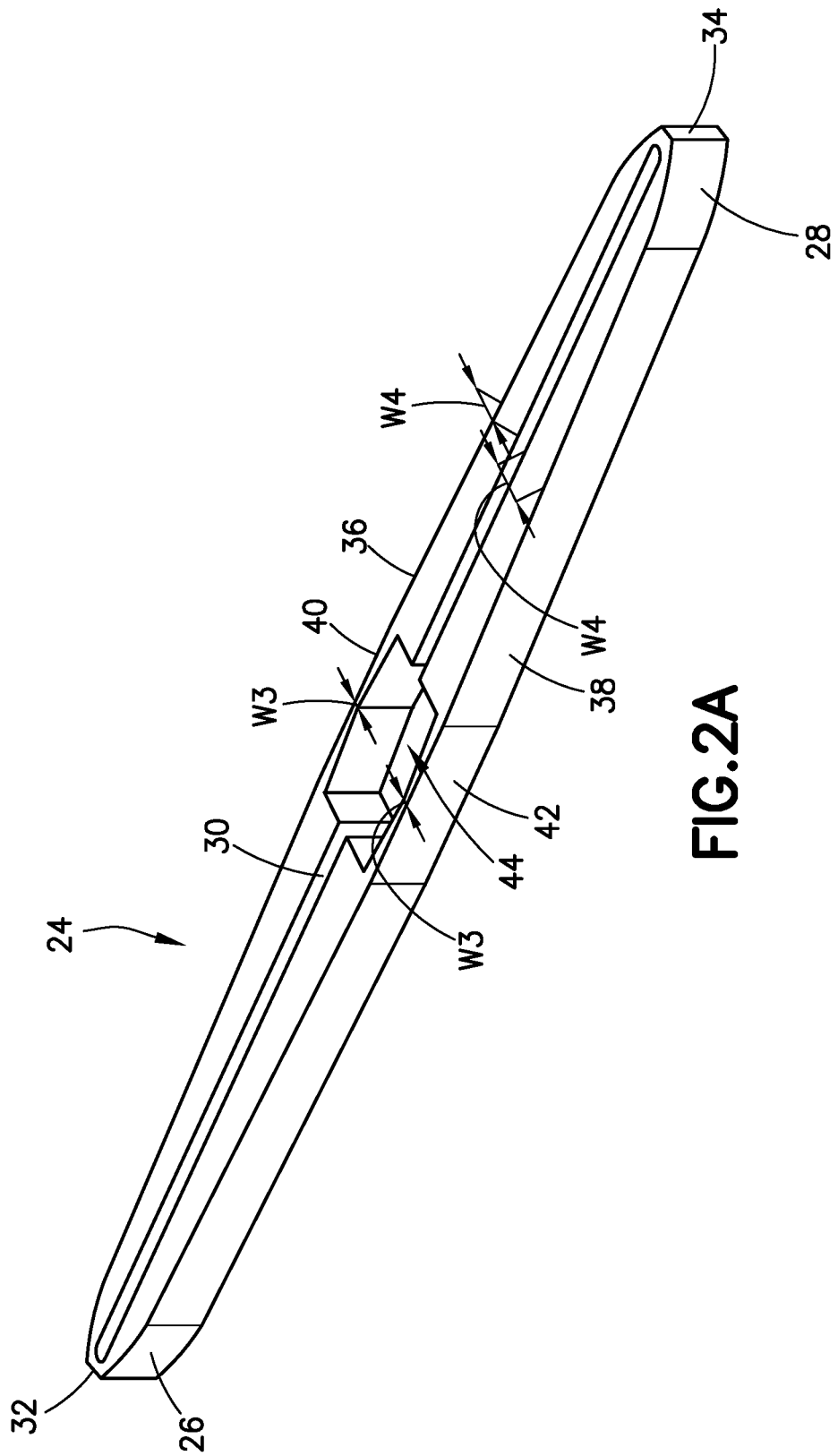

PACKAGE FOR MEDICAL DEVICES INCLUDING A PINCH-OPEN CLOSURE

BACKGROUND OF THE INVENTION

Field of the Invention

The present disclosure relates generally to packaging for medical devices, such as prefilled and/or disposable syringes. More particularly, the present disclosure relates to packaging, such as a package, pouch, gusseted bag, or similar container, including a sealed closure that can be opened with one hand.

Description of Related Art

Medical devices are often provided in sterile barriers, packages, bags, pouches, or containers, which can be opened by a user, such as a practitioner, clinician, or healthcare worker, at a medical treatment location. As used herein, a "healthcare worker" can be a medical professional, such as a medical technician or nurse, trained to perform a medical procedure, such as a fluid delivery or blood collection procedure Current practice for opening medical device packaging, such as a bag or pouch containing a medical device, involves using two hands to grasp portions of the packaging and pull the portions away from each other to open the packaging. However, this practice presents challenges during situations where medical devices must be accessed quickly and/or where space constraints make it difficult to use two hands to hold and manipulate the packaging, such as during treatment of a patient for an emergency condition or at an emergency site. In particular, there can be significant space constraints during treatment of patients for medical emergencies in ambulance environments and in other paramedical scenarios.

Accordingly, there is a need in the art for improved packages and containers that provide a barrier to maintain sterility of medical devices contained therein and are easy to open quickly, even when space is severely constrained. In particular, there is a need for packages and containers that can be opened with one hand, desirably without looking at the packaging. Accordingly, practitioners can continue to perform other tasks and/or to visually monitor the patient while opening the packaging or container to access the medical device(s) contained therein. The packages, containers, and methods of the present disclosure are configured to address these issues.

SUMMARY OF THE INVENTION

According to an aspect of the present disclosure, a package includes a flexible body configured to transition between a collapsed configuration and an expanded configuration. The body includes an open first end, a closed second end, and sides extending between the open first end and the closed second end. The package also includes a closure connected to the body having a first end, a second end, and a slit extending at least partially between the first end and the second end of the closure. The closure is configured to transition between a closed configuration, in which the closure retains the body in the collapsed configuration sealing the open first end of the body, and an open configuration upon application of a biaxial force to the first end and the second end of the closure, which causes the body to transition to the expanded configuration.

According to another aspect of the present disclosure, a method for opening the previously described package includes simultaneously pressing against the first end of the closure and the second end of the closure, thereby causing the closure to move from the closed configuration toward the open configuration.

In accordance with an embodiment of the present invention, a package includes a flexible body configured to transition between a collapsed configuration and an expanded configuration, the body having an open first end, a closed second end, and sides extending between the first end and the second end, and a closure connected to the body having a first end, a second end, and a slit extending at least partially between the first end and the second end of the closure. The closure is configured to transition between a closed configuration, in which the closure retains the body in the collapsed configuration sealing the open first end of the body, and an open configuration upon application of a biaxial force to the first end and the second end of the closure, which causes the body to transition to the expanded configuration.

In accordance with an embodiment of the present invention, with the closure in the open configuration, an interior of the body is accessible through the slit of the closure.

In accordance with an embodiment of the present invention, an outer periphery of the closure is an ellipse or a rectangle.

In accordance with an embodiment of the present invention, when in the open configuration, the closure defines a square, rectangular, or parallelogram shaped opening.

In accordance with an embodiment of the present invention, once moved to the open configuration, the closure remains in the open configuration when the application of the biaxial force ceases.

In accordance with an embodiment of the present invention, the package is configured to contain a medical device, such as a prefilled and/or disposable syringe.

In accordance with an embodiment of the present invention, the body includes polyethylene terephthalate, polypropylene, low-density polyethylene, or combinations thereof.

In accordance with an embodiment of the present invention, the body includes a first sheet and a second sheet of a flexible polymer material sealed together about portions of a periphery of the first sheet and the second sheet, thereby forming the open first end, the closed second end, and the sides of the body.

In accordance with an embodiment of the present invention, a coating includes vinyl acetate over exterior surfaces of the first sheet and/or the second sheet of the body.

In accordance with an embodiment of the present invention, the portions of the periphery of the first sheet and the second sheet are sealed together by heat sealing.

In accordance with an embodiment of the present invention, when the closure is in the closed configuration, the slit of the closure is sealed, thereby sealing the open first end of the body.

In accordance with an embodiment of the present invention, the application of the biaxial force to the first end and the second end of the closure unseals the slit, thereby allowing sides of the closure to move apart causing the body to move to the expanded configuration.

In accordance with an embodiment of the present invention, the closure is embedded in the body and the slit is sealed by heat sealing.

In accordance with an embodiment of the present invention, the closure includes a plastic strip including polypropylene, high density polyethylene, or combinations thereof.

In accordance with an embodiment of the present invention, the first end of the closure includes a first living hinge and the second end of the closure including a second living hinge.

In accordance with an embodiment of the present invention, the closure further includes a first side part extending between the first living hinge and the second living hinge, and a second side part extending between the first living hinge and the second living hinge, and wherein the first side part and the second side part are separated by the slit.

In accordance with an embodiment of the present invention, the first side part includes a first weakened buckling portion and the second side part includes a second weakened buckling portions, and wherein the buckling portions are configured to bend as the closure moves from the closed configuration to the open configuration.

In accordance with an embodiment of the present invention, an angle defined by the first buckling portion or the second buckling portion becomes smaller as the closure moves from the closed configuration to the open configuration.

In accordance with an embodiment of the present invention, a width of the buckling portions is less than a width of other portions of the first side part and the second side part.

In accordance with an embodiment of the present invention, the weakened buckling portions are equidistantly spaced between the first living hinge and the second living hinge.

In accordance with an embodiment of the present invention, the buckling portions are formed by a widened area of the slit.

In accordance with an embodiment of the present invention, the closure is an integrally molded part including the first side part and the second side part connected by the first living hinge and the second living hinge.

In accordance with an embodiment of the present invention, the closure and the first open end of the body are from 15 cm to 21 cm in length.

In accordance with an embodiment of the present invention, a force required to move the closure from the closed configuration to the open configuration is from about 3 N to about 30 N or, preferably, from about 3.3 N to about 17 N.

In accordance with an embodiment of the present invention, a method for opening a package includes simultaneously pressing against the first end of the closure and the second end of the closure, thereby causing the closure to move from the closed configuration toward the open configuration.

In accordance with an embodiment of the present invention, the method includes pressing against the first end of the closure with an index finger of a hand and pressing against the second end of the closure with a thumb of the same hand.

In accordance with an embodiment of the present invention, the method includes removing at least one medical device from an interior of the package when the closure is in the open configuration and the body is in the expanded configuration.

In accordance with an embodiment of the present invention, the method includes allowing the closure to return to the closed configuration by releasing the closure.

In accordance with an embodiment of the present invention, the method includes pressing against the buckling portions of the closure to cause the closure to return to the closed configuration.

BRIEF DESCRIPTION OF THE DRAWINGS

FIG. 2A is a perspective view of the pinch-open closure of FIG. 1A.

DESCRIPTION OF THE INVENTION

Figure 1A:
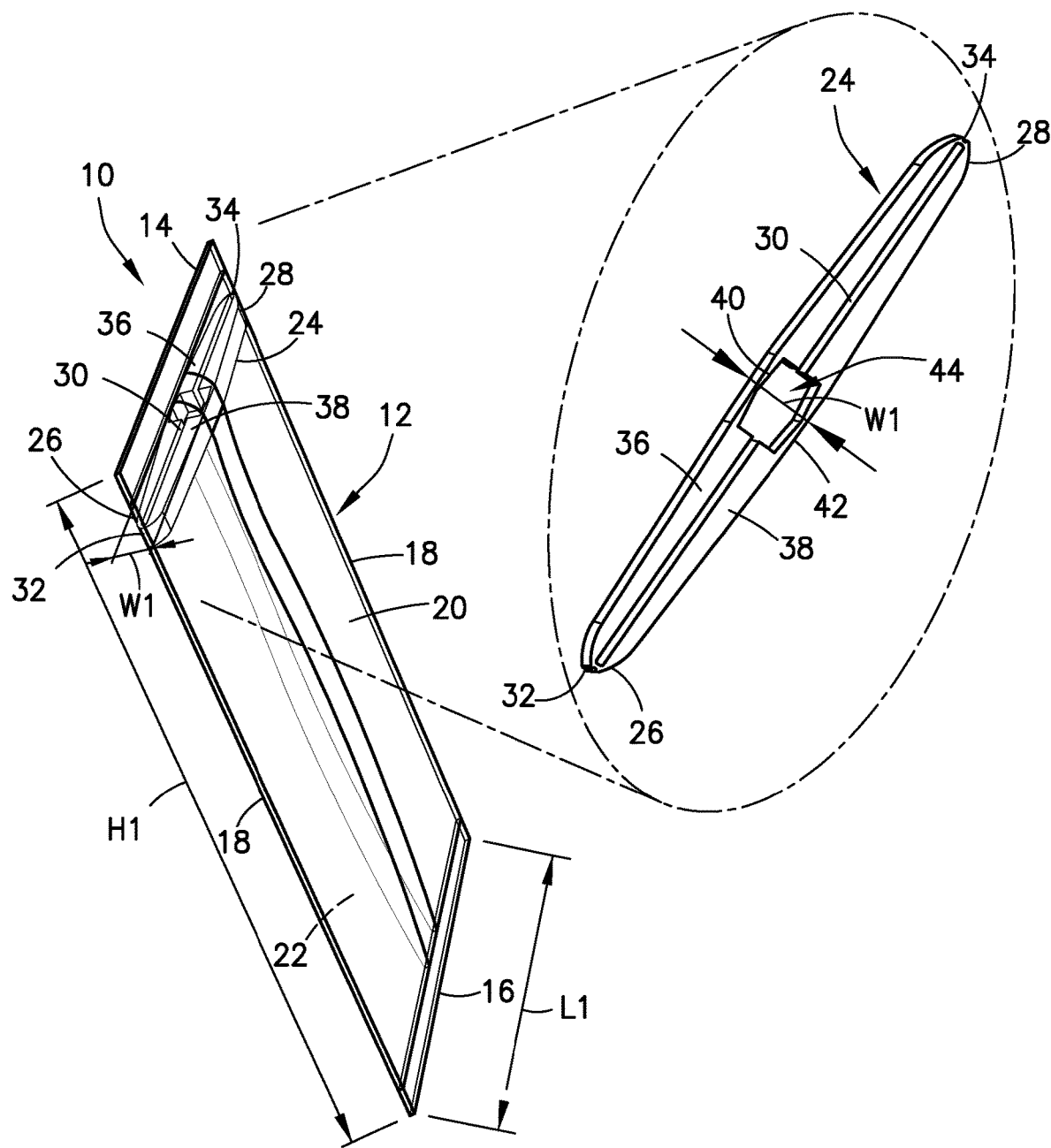
FIG. 1A is a perspective view of a package for a medical device including a pinch-open closure in a closed configuration, according to an aspect of the present disclosure.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting.

With reference to the figures, the present disclosure is directed to medical device packaging, such as packages 10, bags, pouches, enclosures, and similar containers that provide a sterile barrier for tools (e.g., medical devices) used for performing medical procedures, such as fluid delivery procedures, blood draw and fluid collection procedures, and/or vascular access procedures. Medical devices that can be enclosed within the packages 10 or containers of the present disclosure can include, without limitation, surgical tools, syringes (e.g., prefilled and/or disposable syringes), catheters, vascular access devices, intravenous ports, and other disposable or single-use medical devices used for commonly performed medical procedures, as are known in the art.

As will be appreciated by those skilled in the art, the packages 10 of the present disclosure can provide a single easily transportable item that can be quickly obtained from a storage area and carried to a patient's bedside to perform a medical procedure. Further, the packages 10 of the present disclosure can reduce a risk of infection, improve quality of collected samples, and increase efficiency of medical procedures by ensuring that tools needed for performing a medical procedure are maintained in a sterile condition until ready for use.

The packages 10 of the present disclosure are designed to be easy for practitioners, such as medical technicians, nurses, physician assistants, physicians, or other trained, or untrained clinicians or medical caregivers, to manipulate and open avoiding unnecessary delays in accessing medical devices contained in the packages 10. In some particularly advantageous examples, the packages 10 of the present disclosure can be opened by the practitioner with one hand. Further, the packages 10 can be opened by touching only a small area of an external surface of the package 10, making it less likely that the practitioner will touch or contaminate other interior or exterior areas or surfaces of the package 10 or of the medical device(s) contained therein. Specifically, the practitioner desirably should be able to open the package 10 with one hand by manipulating only a first or top end of the package 10 proximate to an opening of the package 10. By contrast, for conventional pouches or bags, as previously described, the practitioner may need to grasp the package with two hands and/or may need to contact a larger area of an outer surface of the package to open to package and to remove the medical device from the package.

In some examples, the packages 10 disclosed herein are configured to be manufactured using existing production lines and without affecting production time for the existing production lines. For example, the packages 10 of the present disclosure can be manufactured by applying an additional closure, strip, or seal to existing packages, which can be accomplished by adding a single assembly step performed with the existing production lines. Accordingly, the packages 10 can be convenient to manufacture, thereby obtaining the benefits of improved sealing, reduced risk of contamination, and single-handed operation, without significantly impacting existing production processes.

Medical Device Packaging

Figure 1B:
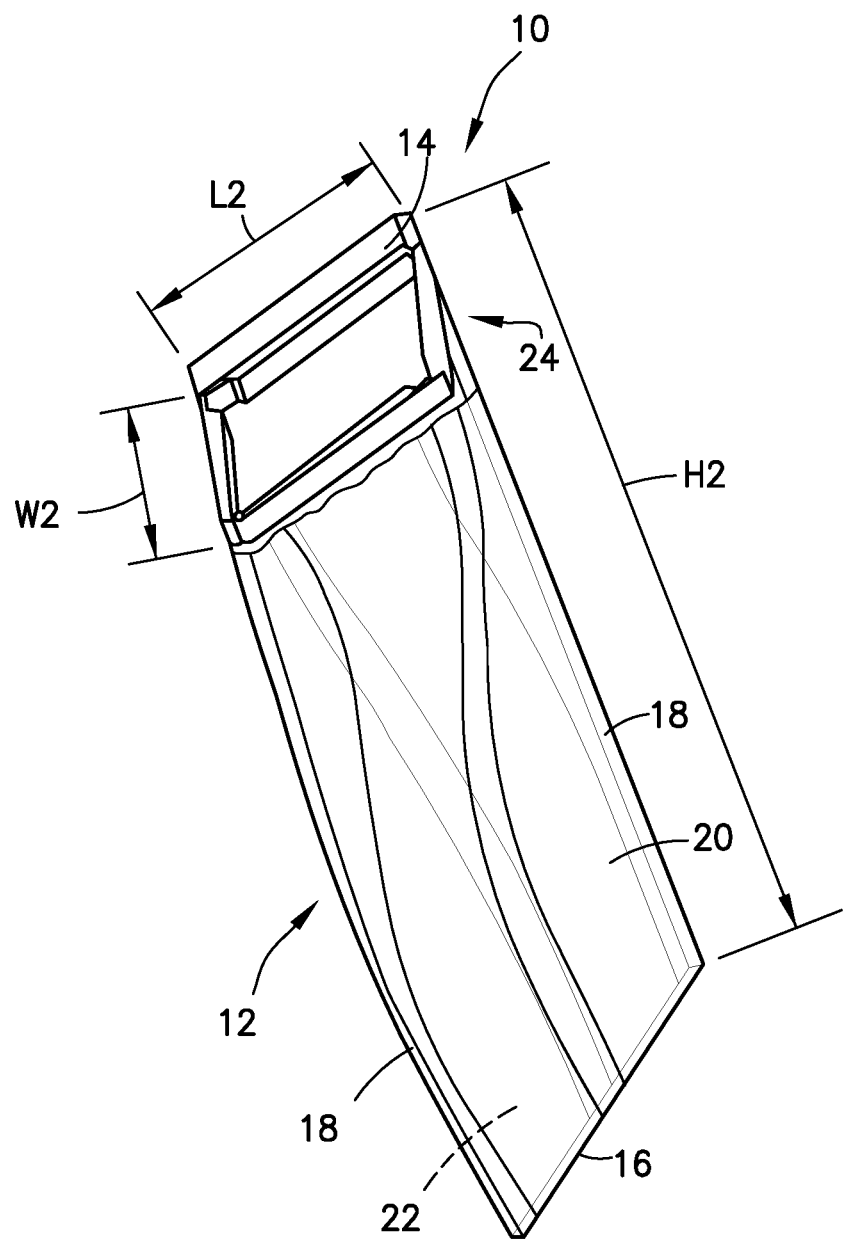
FIG. 1B is a perspective view of the package of FIG. 1A including the pinch-open closure in an open configuration, according to an aspect of the present disclosure.

With reference to FIGS. 1A and 1B, a package 10, such as a pouch, bag, or similar container, configured to contain a medical device (not shown), such as a vascular access device or syringe (e.g., a disposable and/or prefilled syringe), comprises a flexible pouch, bag, or body 12 configured to transition between a collapsed configuration (shown in FIG. 1A) and an expanded configuration (shown in FIG. 1B). For example, the body 12 can be a pouch or bag formed from a flexible synthetic or natural fabric, film, or sheet, such as a plastic sheet (e.g., a sheet comprising polyethylene terephthalate, polypropylene, low-density polyethylene, or combinations thereof), paper, cloth, or similar materials. As shown in FIG. 1A, in the collapsed configuration, the body 12 can be substantially flat. The body 12 expands to the expanded configuration (shown in FIG. 1B), in which the body 12 conforms to a three-dimensional shape sized to receive the medical device.

In some examples, the body 12 includes a first or open end 14, a second or closed end 16, and sides 18 extending between the open end 14 and the closed end 16. As described in further detail herein, dimensions of the body 12 are selected so that the body 12 can be easily manipulated by the practitioner with one hand. In some non-limiting examples, in the collapsed configuration (shown in FIG. 1A), the body 12 can have a height H1 of about 8.0 cm to about 21.0 cm, a length L1 of about 12.0 cm to about 15.0 cm, and a width W1 of about 0.35 cm to about 1.0 cm. In the expanded configuration (shown in FIG. 1B), the height H2 remains about the same, while the length L2 decreases, and the width W2 increases. For example, in the expanded configuration (shown in FIG. 1B), the body 12 can have a height H2 of about 8.0 cm to about 21.0 cm, a length L2 of about 10.0 cm to about 13.0 cm, and a width W2 of about 2.35 cm to about 3.0 cm.

The bag or body 12 of the present disclosure can comprise a variety of different types of pouch or flow-wrap designs made through conventional manufacturing processes. In some examples, portions of the pouch and/or flow-wrap can be the polymeric materials, such as polymeric materials that are laminated or mono-layered with internal sealing through application of heat. A sealant for the pouch and/or flow-wrap can be a scalable polymer material, such as low density polyethylene (LDPE) or an ethylene-vinyl acetate (EVA) additive structures.

In some examples, the body 12 can be formed from a first or top sheet 20 and a second or bottom sheet 22 of a flexible polymer material (e.g., polyethylene terephthalate, polypropylene, or low-density polyethylene) sealed together about portions of a periphery of the top sheet 20 and the bottom sheet 22 to form the open end 14, the closed end 16, and closed or sealed sides 18 of the body 12. For examples, the sheets 20, 22 can be adhered together by heat sealing, or with an adhesive applied near the periphery of the sheets 20, 22, to form a seal or seam between the sheets 20, 22. In some examples, the sheets 20, 22 can be coated with a protective material, such as layers of a vinyl acetate material deposited over exterior surfaces of the top sheet 20 and/or the bottom sheet 22 of the body 12. Other types of polymer materials can also be applied to the package 10 for aesthetic purposes and/or to protect the medical devices contained in the package 10. In some examples, labels, and other identifying indicia, can also be applied to or printed on surface(s) of the sheets 20, 22 to identify the medical device(s) contained in the package 10. Desirably, any coating layers or materials on the sheets 20, 22 does not prevent labels and other adhesives from being adhered to the sheets 20, 22.

Figure 2C:
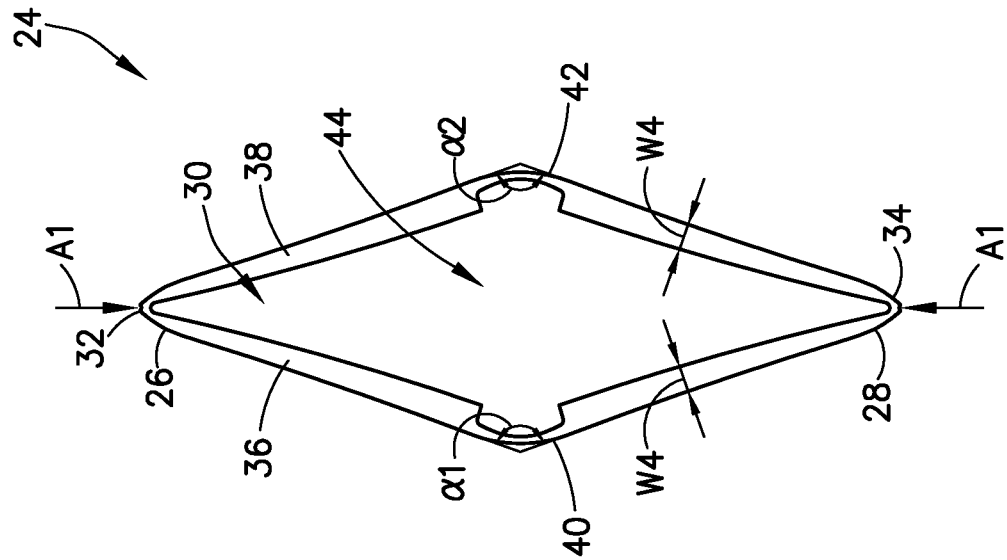
FIG. 2C is a top view of the pinch-open closure of FIG. 1A in the open configuration.
Figure 2B:
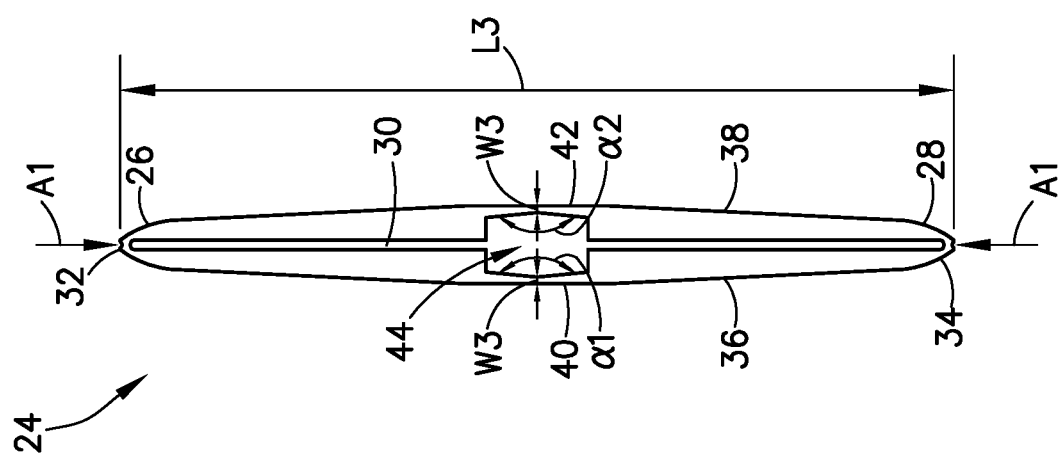
FIG. 2B is a top view of the pinch-open closure of FIG. 1A in the closed configuration.

With reference to FIGS. 1A and 1B, as well as FIGS. 2A-2C, the package 10 further comprises a pinch-open closure 24, such as an elongated member or plastic strip, connected to the body 12. The closure 24 can comprise a first end 26, a second end 28, and a slit 30 extending at least partially between the first end 26 and the second end 28 of the closure 24. The closure 24 can be formed from a rigid thermoplastic material, such as a homopolymer comprising polypropylene or high density polyethylene.

The closure 24 is configured to transition between a closed configuration (shown in FIGS. 1A, 2A, and 2B) and an open configuration (shown in FIGS. 1B and 2C). In some examples, an outer periphery of the closure 24, in the closed configuration, is elliptical in shape, as shown in FIGS. 1A, 2A, and 2B. In other examples, as shown in FIGS. 3A-4B, the periphery of the closure 24, in the closed configuration, can be rectangular. In the closed configuration, the closure 24 retains the pouch, bag, or body 12 of the package 10 in the collapsed configuration, scaling the open end 14 of the body 12. Specifically, the slit 30 of the closure 24 can be sealed (e.g., sealed by the heat sealing process), providing a barrier that prevents contamination of the medical devices(s) contained in the package 10. Upon application of a biaxial force to the first end 26 and the second end 28 of the closure 24, the closure 24 moves toward an open configuration. Movement of the closure 24 to the open configuration causes the body 12 of the package 10 to transition to the expanded configuration. When the closure 24 is open and the body 12 is in the expanded configuration, an interior of the pouch, bag, or body 12 is accessible through the slit 30 of the closure 24, which expands to conform to a shape of the open end 14 of the body 12.

The closure 24 can be configured to support the open end 14 of the body 12 in a variety of shapes and configurations. For example, as shown in FIGS. 1B and 2C, the open closure 24 is a parallelogram having legs that intersect forming angles that are not 90 degrees. In some examples, all four legs of the parallelogram can be the same length, as shown in FIG. 2C. In other examples, the parallelogram can include two short legs and two longer legs, as shown in FIG. 1B. In other examples, the closure 24 can be configured to maintain a variety of other shapes, including a square, rectangle, diamond, an irregular polygon shape, ellipse, oval, or circle, within the scope of the present disclosure.

As used herein, the "biaxial force" applied to the closure 24 refers to axial forces that are simultaneously applied to an elongated member in opposite directions. For example, inwardly directed axial forces can be applied to the ends 26, 28 of the closure 24, as shown by arrows A1 in FIGS. 2B and 2C, in order to cause the closure 24 to transition from the closed configuration to the open configuration.

As shown in FIGS. 1A and 1B, the closure 24 is connected to the body 12 proximate to the open end 14 of the body 12. In some examples, the closure 24 can be embedded in the body 12. For example, layers or sheets of plastic material can be laminated over or around surfaces of the closure 24, thereby securing the closure 24 to the body 12.

In other examples, the closure 24 can be connected to the body 12 using a conventional adhesive, as is known in the art. For example, a peripheral surface of the closure 24 can be adhered to inner surfaces of sheets 20, 22 of the body 12 by applying a small amount of the adhesive to the surfaces of the closure 24 and body 12 and then curing or drying the adhesive to seal the closure 24 to the body 12. In other examples, the sheets 20, 22 that form the body 12 can be inserted through the slit 30 of the closure 24, such that the outer surfaces of the sheets 20, 22 are adhered to the inner surface of the slit 30.

In some examples, the fixture or closure 24 can be attached to an inside of body 12 during formation of the package 10 and prior to sealing portions of the sheets 20, 22 together creating a sealed package 10. In particular, the fixture or closure 24 can be fixed within the body 12 below the sealed portion of the body 12. The closure 24 can be held in place by applying heat to the body 12 while polymeric films of the body 12 are laminated around the closure 24. Alternatively or in addition, the adhesive can be applied between the closure 24 and the body 12, as the body 12 is being laminated, to adhere the closure 24 to the body 12. The sheets 20, 22 of the body 12 are then sealed at a position above the closure 24 to form the sealed package 10.

In some examples, portions of the closure 24 can be biased to the open configuration, meaning that, once partially opened, the closure 24 can automatically move to a fully opened configuration (as shown in FIG. 2C) without requiring the practitioner to continue to apply the biaxial force to the closure 24. Further, in some examples, the closure 24 can be configured to remain in the fully opened configuration even after application of the biaxial force to the closure 24 ceases.

As shown in FIGS. 2A-2C, in some examples, the closure 24 comprises living hinges 32, 34 at the ends 26, 28 of the closure 24 with axially-extending segments or parts 36, 38 extending between the living hinges 32, 34 and separated by the slit 30. As used herein, a "living hinge" refers to a hinge formed from a thin flexible segment or portion of an object made of a same material as two more rigid portions or segments of the object connected by the thin flexible living hinge. The living hinge is capable of bending to open and close in a similar manner to hinges formed between separate rigid pieces connected to a post, pin, or rotation point. For example, as shown in FIGS. 2A-2C, the closure 24 includes the living hinges 32, 34 extending between the rigid axially-extending segments or parts 36, 38 of the closure 24.

In some examples, the closure 24 also includes notches, grooves, recesses, or gaps, which form weakened buckling portions 40, 42 of the segments or parts 36, 38, positioned between the living hinges 32, 34. The weakened buckling portions 40, 42 are portions of the closure 24 that bend or deform as the closure 24 moves between the closed configuration (in FIGS. 2A and 2B) and the open configuration (in FIG. 2C). In particular, the buckling portions 40, 42 can be narrow flexible segments between wider, more rigid, segments of the parts 36, 38. The buckling portions 40, 42 can form angles (shown by angles $\alpha 1$ and $\alpha 2$ in FIGS. 2B and 2C) that close (e.g., become smaller) as the closure 24 moves from the closed configuration to the open configuration. For example, as shown in FIG. 2B, the angles $\alpha 1$, $\alpha 2$ in the open configuration can be nearly 180 degrees. As the closure 24 moves to the open configuration, the angles $\alpha 1$, $\alpha 2$ can approach, for example, 120 degrees, 100 degrees, or 90 degrees, as shown in FIG. 2C.

The buckling portions 40, 42 can be formed from a bulbous or widened area 44 of the slit 30 positioned such that a width W3 (shown in FIGS. 2A and 2B) of the buckling portions 40, 42 is less than a width W4 (shown in FIGS. 2A and 2B) of other portions of the segments or part 36, 38. For example, the width W3 of the buckling portions 40, 42 can be about 0.3 mm to about 0.7 mm. The width W4 of other portions of the segments or parts 36, 38 can be about 3.0 mm to about 5.0 mm.

Positioning of the buckling portions 40, 42 on the parts 36, 38 affects the shape of the closure 24 in the open configuration. For example, as shown in FIGS. 2A-2C, the closure 24 can include a buckling portion 40, 42 on each of the segments or parts 36, 38 of the closure 24. The buckling portions 40, 42 can be equidistantly spaced or substantially equidistantly spaced between the ends 26, 28 of the closure 24, such that in the open configuration, the closure 24 forms a square or parallelogram with substantially equal length legs, as shown in FIG. 2C. Alternatively, the buckling portions 40, 42 can be positioned closer to one of the ends 26, 28 of the closure 24 than the other end, such that, when expanded, the closure 24 forms a rectangle or parallelogram with two short legs and two long legs, as shown in FIG. 1B.

In some examples, the closure 24 can be made by conventional molding methods, as are known in the art. For example, the closure 24 can be an integral part comprising the living hinges 32, 34 and segments or parts 36, 38 formed together by a same material in a single injection molding process.

In some examples, dimensions and mechanical features of the closure 24 are selected so that the package 10 can be easily and comfortably opened by an average-sized adult individual applying a reasonable pinching force to the ends 26, 28 of the closure 24 with one hand. In particular, a length L3 (shown in FIG. 2B) of the closure 24, in the closed configuration, can be selected based on an average distance between index finger and thumb for an adult, which has been found to be about 18 cm. For example, the length L3 of the closure 24, in the closed configuration, can be about 15 cm to about 21 cm. In other examples, the length L3 of the closure 24 can be less than 18 cm or, preferably less that about 15 cm to accommodate practitioners with slightly smaller than average hand size. Similarly, the force required to move the closure 24 from the closed configuration to the open configuration can be selected taking into account a maximum pinching force that an average adult can comfortably provide between a finger and thumb, which has been found to be about 60 N for men and about 45 N for women. Therefore, the maximum force required to cause the closure 24 to open can be less than or substantially less than 45 N. For example, the closure 24 can be configured to open when a force of about 3.3 N to about 17 N, or preferably about 3 N to about 12 N, is applied to the ends 26, 28 of the closure 24 to accommodate practitioners with less than average pinch and/or grip strength.

Figure 3B:
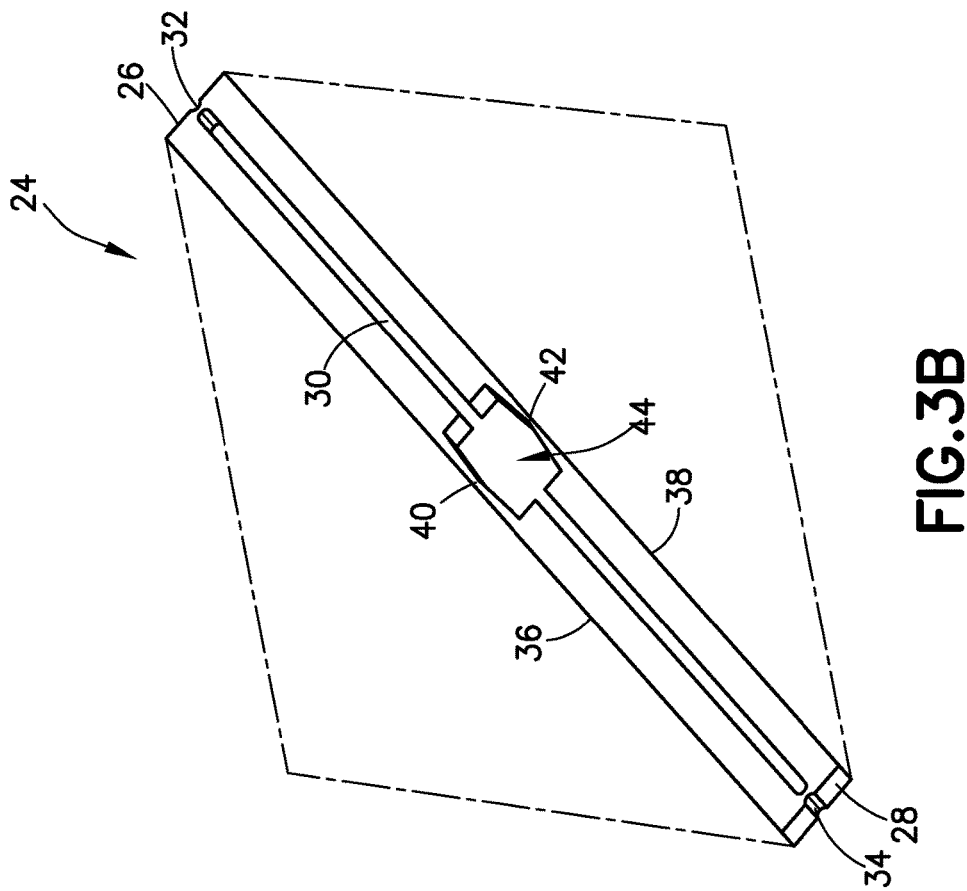
FIG. 3B is another perspective view of the pinch-open closure of FIG. 3A.
Figure 3A:
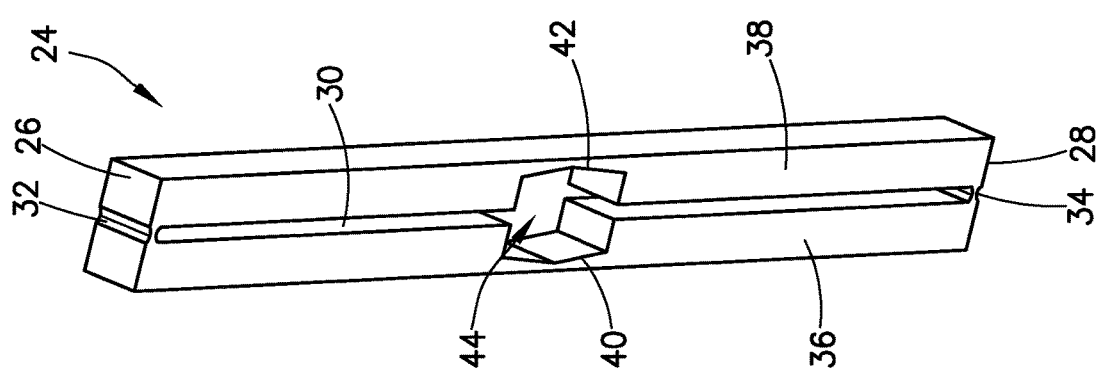
FIG. 3A is a perspective view of another example of a pinch-open closure, according to an aspect of the present disclosure.

FIGS. 3A and 3B show another example of a closure 24 that can be used with the package 10 of the present disclosure. For example, the closure 24 of FIGS. 3A and 3B can be used for gusseted bags. By contrast, in previous examples of FIGS. 2A-2C, the bag or body 12 of the package 10 is a pouch. The closure 24 of FIGS. 3A and 3B is similar to previous examples and, in particular, includes an elongated member having a first end 26, a second end 28, and the axially-extending segments or parts 36, 38 extending between the first end 26 and the second end 28. The closure 24 also includes the slit 30 which forms a gap or space between the segments or parts 36, 38 of the closure 24. The closure 24 also includes the living hinges 32, 34.

As in previous examples, the closure 24 is configured to transition between a closed configuration and an open configuration. In the closed configuration, the closure 24 retains a bag, pouch, or body 12 of the package 10 in a collapsed configuration. Upon application of a biaxial force to the first end 26 and the second end 28 of the closure 24, the closure 24 transitions to the open configuration. As previously described, causing the closure 24 to move from the closed configuration to the open configuration causes the body 12 of the package 10 to transition to the expanded configuration.

Unlike in previous examples, the closure 24, shown in FIGS. 3A and 3B, has a rectangular shaped periphery in the closed configuration. Further, the segments or parts 36, 38 of the closure 24 are substantially straight. By contrast, in previous examples (shown in FIGS. 1A-2C), the periphery of the closure 24 is elliptical and the outer edges of the segments or parts 36, 38 are curved. In some cases, a rectangular shaped closure 24 may be easier to mold and manufacture than closures 24 having a complex curvature. Accordingly, the closure 24 of FIGS. 3A and 3B may be preferred to simplify manufacturing.

Method of Opening a Medical Package

As previously described, the packages 10 of the present disclosure will generally be provided pre-filled with one or more medical devices intended for use for a medical procedure. For example, the packages 10 can contain one or more syringes (e.g., a disposable and/or prefilled syringe) or another type of vascular access device. As previously described, the exemplary packages 10 and closures 24 disclosed herein are intended to be easy to manipulate and open so that practitioners can obtain medical devices and tools contained in the packages 10 without disrupting other aspects of a medical procedure being performed for a patient. For example, the packages 10 can be opened with one hand and, in some cases, without looking at the package 10 and closure 24 so that the practitioner can continue to perform other tasks and/or can continue to visually monitor the patient while opening the package 10.

Figure 4B:
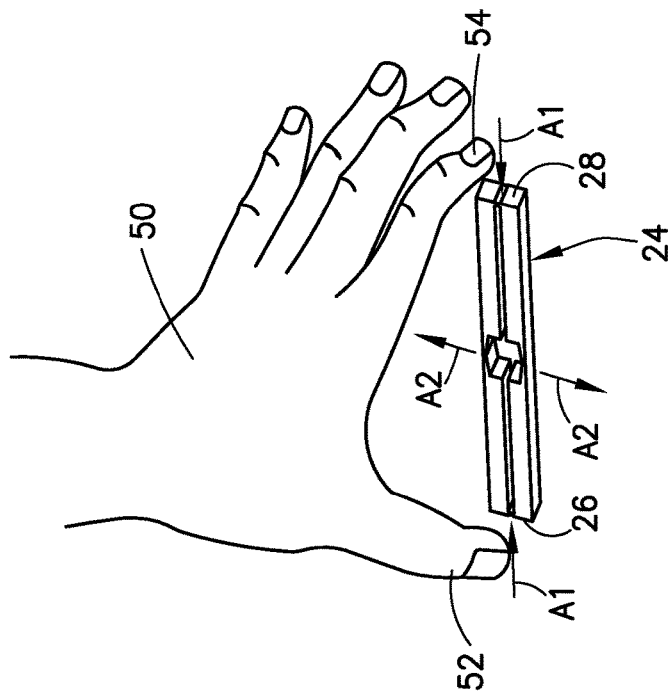
FIG. 4B is a schematic drawing showing the practitioner's hand in proximity to a pinch-open closure, according to an aspect of the present disclosure.
Figure 4A:
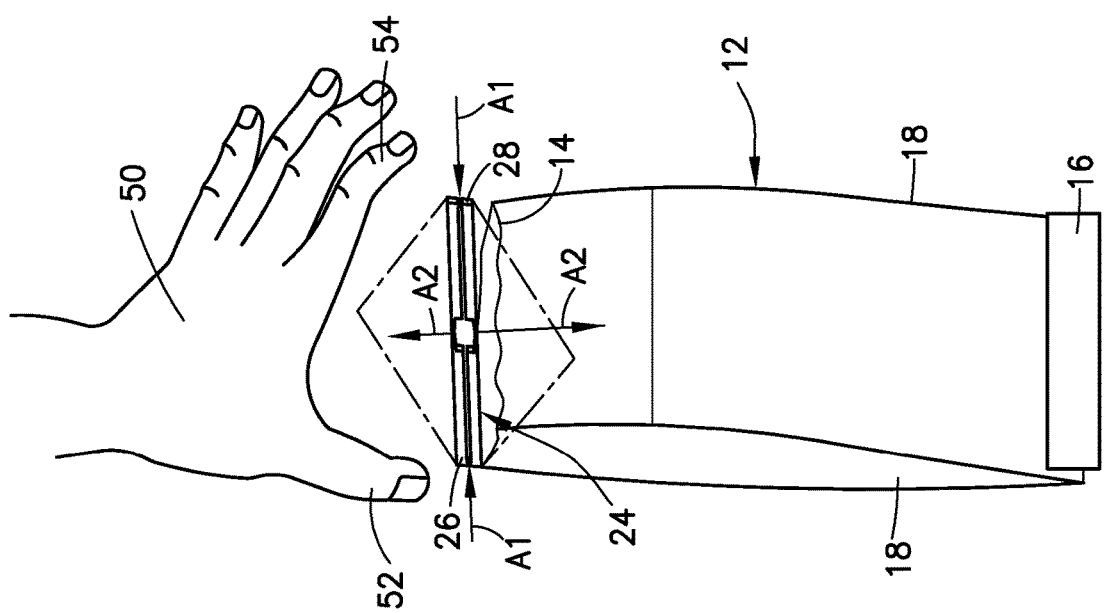
FIG. 4A is a schematic drawing showing a practitioner's hand in proximity to a package for a medical device, according to an aspect of the present disclosure.

FIGS. 4A and 4B are schematic drawings showing the package 10 being grasped by a practitioner to open the package 10. A method for opening the package 10 can include the following steps. Initially, when ready for use, the practitioner grasps the package 10 in one hand 50 and simultaneously presses against the first end 26 of the closure 24 and the second end 28 of the closure 24, as shown by arrows A1 in FIGS. 4A and 4B. For example, the practitioner can grasp the package 10 between the thumb 52 and index finger 54, with the thumb 52 positioned proximate to the first end 26 of the closure 24, and the index finger 54 positioned proximate to the second end 28 of the closure 24.

The practitioner then performs a pinching motion moving the index finger 54 and the thumb 52 towards one another to apply the biaxial force to the opposing ends 26, 28 of the closure 24. An initial amount of biaxial force may be sufficient to overcome or release a seal between the segments or parts 36, 38 of the closure 24. Once the seal releases, the practitioner continues to apply the biaxial force to the closure 24, which causes the segments or parts 36, 38 of the closure 24 to move away from each other, as shown by arrow A2 in FIGS. 4A and 4B. The biaxial force applied to the closure 24 ultimately causes the closure 24 to move from the closed configuration toward the open configuration.

As previously described, as the closure 24 moves to the open configuration, the buckling portions 40, 42 of the closure 24 bend or deform causing the closure 24 to adopt a shape of a square, rectangle, or parallelogram. Also, moving the closure 24 to the open configuration causes the bag or body 12 of the package 10 to move to the expanded configuration. Once the closure 24 is in the open configuration and the body 12 is expanded, the practitioner can remove the medical device from the package 10 through the open end 14 of the body 12 and through the open closure 24.

Once the desired item is removed from the package 10, the practitioner can close the package 10. If the closure 24 is biased to the closed configuration, the practitioner can simply release the closure 24, allowing the closure 24 to automatically return to the closed configuration. Alternatively, if the closure 24 is not biased to the closed configuration, the practitioner can either pull the ends 26, 28 of the closure 24 away from each other or apply a biaxial force to the buckling portions 40, 42 of the closure 24, thereby causing the closure 24 to return to the closed configuration. As the closure 24 moves to the closed configuration, the bag or body 12 of the package 10 returns to a more contracted or compressed configuration as shown, for example, in FIG. 1A.

While examples of the packages 10, containers, and methods are shown in the accompanying figures and described hereinabove in detail, other examples will be apparent to, and readily made by, those skilled in the art without departing from the scope and spirit of the invention. Accordingly, the foregoing description is intended to be illustrative rather than restrictive. The invention described hereinabove is defined by the appended claims and all changes to the invention that fall within the meaning and the range of equivalency of the claims are to be embraced within their scope.

The invention claimed is:

1. A package for at least one medical device comprising a vascular access device, a disposable syringe, and/or a prefilled syringe, the package comprising:
   a flexible body configured to contain the at least one medical device and to transition between a collapsed configuration and an expanded configuration, the flexible body comprising an open first end, a closed second end, and sides extending between the first end and the second end; and
   a closure connected to the flexible body comprising:
      a first end, a second end,
  at least one slit extending at least partially between the first end and the second end of the closure,
  a first buckling portion on one side of the at least one slit, and
  a second buckling portion on an opposing side of the at least one slit, wherein the buckling portions define an opening with longitudinal sides that are angled outwardly relative to a longitudinal axis of the closure, such that, for each longitudinal side, a shortest distance between an intermediate point of the longitudinal side and the longitudinal axis of the closure is greater than a shortest distance between ends of the longitudinal sides and the longitudinal axis of the closure,
  wherein the closure is configured to transition between a first configuration, in which the closure retains the flexible body in the collapsed configuration preventing removal of the at least one medical device from the flexible body through the open first end, and a second configuration, which permits removal of the at least one medical device from the flexible body through the at least one slit of the closure, upon application of a biaxial force to the first end and the second end of the closure, which causes the flexible body to transition to the expanded configuration.

2. The package of claim 1, wherein an outer periphery of the closure is an ellipse or a rectangle.

3. The package of claim 1, wherein, when in the second configuration, the closure defines a square, rectangular, or parallelogram shaped opening, and
  wherein, once moved to the second configuration, the closure remains in the second configuration when the application of the biaxial force ceases.

4. The package of claim 1, wherein the body comprises polyethylene terephthalate, polypropylene, low-density polyethylene, or combinations thereof, and
  wherein the closure comprises a plastic strip comprising polypropylene, high density polyethylene, or combinations thereof.

5. The package of claim 1, wherein the body comprises a first sheet and a second sheet of a flexible polymer material sealed together about portions of a periphery of the first sheet and the second sheet, thereby forming the open first end, the closed second end, and the sides of the body.

6. The package of claim 5, further comprising a coating comprising vinyl acetate over exterior surfaces of the first sheet and/or the second sheet of the body.

7. The package of claim 5, wherein the transition of the closure from the first configuration to the second configuration causes portions of the first sheet, which are not sealed to the second sheet, to move away from the second sheet.

8. The package of claim 1, wherein the first end of the closure comprises a first living hinge and the second end of the closure comprises a second living hinge.

9. The package of claim 8, wherein the closure further comprises a first side part extending between the first living hinge and the second living hinge, and a second side part extending between the first living hinge and the second living hinge, and
  wherein the first side part and the second side part are separated by the at least one slit and by the opening defined by the first and second buckling portions.

10. The package of claim 9, wherein the first side part comprises the first buckling portion and the second side part comprises the second buckling portion, and
  wherein the buckling portions are configured to bend as the closure moves from the first configuration to the second configuration.

11. The package of claim 10, wherein a width of the buckling portions is less than a width of other portions of the first side part and the second side part, and
  wherein the closure is an integrally molded part comprising the first side part and the second side part connected by the first living hinge and the second living hinge.

12. The package of claim 8, wherein the first living hinge and the second living hinge are biased so that the closure remains in the second configuration after the biaxial force applied to the first end and the second end of the closure is removed.

13. The package of claim 1, wherein the closure and the first open end of the body are from about 15 cm to about 21 cm in length.

14. The package of claim 1, wherein a force required to move the closure from the first configuration to the second configuration is from about 3 N to about 30 N.

15. The package of claim 1, wherein the opening defined by the first and second buckling portions further comprises transverse sides, and
  wherein a first segment of the at least one slit extends from a transverse side of the opening toward the first end of the closure and a second segment of the at least one slit extends from an opposing transverse side of the opening toward the second end of the closure.

16. The package of claim 1, wherein angles defined by the first buckling portion and the second buckling portion become smaller as the closure moves from the first configuration to the second configuration.

17. The package of claim 1, wherein the opening defined by the first buckling portion and the second buckling portion comprises a through-hole extending through the closure.

18. A method for accessing at least one medical device contained within the package of claim 1 by opening the package, the method comprising:
  simultaneously pressing against the first end of the closure and the second end of the closure, thereby causing the closure to move from the first configuration toward the second configuration; and
  with the closure in the second configuration, removing the at least one medical device from an interior of the flexible body through the at least one slit.

19. The method of claim 18, comprising pressing against the first end of the closure with an index finger of a hand and pressing against the second end of the closure with a thumb of the same hand.

* * * * *